(12) United States Patent
Advani et al.

(10) Patent No.: US 10,481,105 B2
(45) Date of Patent: Nov. 19, 2019

(54) MEASUREMENT DEVICE AND METHOD FOR ESTIMATING YIELD OF A HARVESTED CROP

(71) Applicant: Deere & Company, Moline, IL (US)

(72) Inventors: Gurmukh H. Advani, West Fargo, ND (US); Noel W. Anderson, Fargo, ND (US); Michael L. Rhodes, Richfield, MN (US); Nikolai R. Tevs, Daytona Beach Shores, FL (US)

(73) Assignee: DEERE & COMPANY, Moline, IL (US)

( * ) Notice: Subject to any disclaimer, the term of this patent is extended or adjusted under 35 U.S.C. 154(b) by 13 days.

(21) Appl. No.: 15/427,298

(22) Filed: Feb. 8, 2017

(65) Prior Publication Data

US 2018/0059034 A1 Mar. 1, 2018

Related U.S. Application Data

(60) Provisional application No. 62/382,115, filed on Aug. 31, 2016.

(51) Int. Cl.
*G01N 22/00* (2006.01)
*H04L 5/00* (2006.01)
(Continued)

(52) U.S. Cl.
CPC ......... *G01N 22/00* (2013.01); *A01D 41/1271* (2013.01); *A01D 41/1272* (2013.01);
(Continued)

(58) Field of Classification Search
CPC .............. A01D 41/127; A01D 41/1271; A01D 41/1272; A01D 45/00; A01D 45/02;
(Continued)

(56) References Cited

U.S. PATENT DOCUMENTS 4,234,882 A 11/1980 Thompson
4,311,957 A 1/1982 Hewitt et al.
(Continued)

FOREIGN PATENT DOCUMENTS

EP 843959 A1 5/1998
EP 940656 A1 9/1999
(Continued)

OTHER PUBLICATIONS

Yeow, Y.K. et al. "Application of Microwave Moisture Sensor for Determination of Oil Palm Fruit Ripeness." Measurement Science Review, vol. 10, No. 1, 2010. Feb. 3, 2010.
(Continued)

*Primary Examiner* — Hoai-An D. Nguyen

(57) ABSTRACT

The measurement device comprises a transmitter for providing a transmitted signal at a frequency. The transmitter provides the transmitted signal to the transmitting antenna. A receiving antenna is arranged to receive the transmitted signal. A receiver is capable of receiving the transmitted signal from the receiving antenna. An electronic data processor is adapted to measure an observed parameter of the transmitted signal between the transmitting antenna and the receiving antenna to estimate the precise yield, where the observed parameter comprises observed attenuation, phase or both of the transmitted signal, as received at the receiver.

18 Claims, 16 Drawing Sheets

(51) Int. Cl.
*A01D 41/127* (2006.01)
*A01D 75/00* (2006.01)
*G01F 1/76* (2006.01)
*G01F 25/00* (2006.01)
*G01F 1/66* (2006.01)
*G01F 1/74* (2006.01)
*G01F 22/00* (2006.01)
*H04B 17/318* (2015.01)
*A01D 45/02* (2006.01)

(52) U.S. Cl.
CPC .............. *A01D 75/00* (2013.01); *G01F 1/66* (2013.01); *G01F 1/662* (2013.01); *G01F 1/666* (2013.01); *G01F 1/74* (2013.01); *G01F 1/76* (2013.01); *G01F 22/00* (2013.01); *G01F 25/003* (2013.01); *H04L 5/0048* (2013.01); *A01D 45/021* (2013.01); *H04B 17/318* (2015.01)

(58) Field of Classification Search
CPC ........ A01D 45/021; A01D 75/00; G01F 1/66; G01F 1/662; G01F 1/666; G01F 1/74; G01F 1/76; G01F 25/003; G01F 22/00; G01N 22/00; H04B 17/318; H04B 5/0048
USPC ....... 324/600, 629, 637, 638, 639, 642, 647, 324/658, 663, 665, 667, 672, 674, 679, 324/681, 683, 686, 691, 709, 76.11, 324/76.39, 76.52, 76.77
See application file for complete search history.

(56) References Cited

U.S. PATENT DOCUMENTS

| | | | |
|---|---|---|---|
| 4,443,792 A | 4/1984 | Pidgeon et al. | |
| 4,782,282 A | 11/1988 | Bachman | |
| 4,806,847 A | 2/1989 | Atherton et al. | |
| 5,057,848 A * | 10/1991 | Rankin | G01R 1/06766 324/140 R |
| 5,233,352 A | 8/1993 | Cournane | |
| 5,529,537 A | 6/1996 | Johnson | |
| 5,609,059 A | 3/1997 | McEwan | |
| 5,770,865 A | 6/1998 | Steffen et al. | |
| 5,957,773 A | 9/1999 | Olmsted et al. | |
| 6,986,294 B2 | 1/2006 | Fromme et al. | |
| 7,068,050 B2 | 6/2006 | Steele et al. | |
| 8,410,793 B2 | 4/2013 | Armbruster et al. | |
| 9,924,636 B2 * | 3/2018 | Lisouski | A01B 69/008 |
| 9,949,435 B2 | 4/2018 | Conrad et al. | |
| 10,188,037 B2 | 1/2019 | Bruns et al. | |
| 2004/0031335 A1 | 2/2004 | Fromme et al. | |
| 2004/0183718 A1 | 9/2004 | Hagg | |
| 2005/0026662 A1 * | 2/2005 | Fechner | A01D 41/1271 460/1 |
| 2006/0240884 A1 | 10/2006 | Klimmer | |
| 2007/0106172 A1 * | 5/2007 | Abreu | A61B 5/0002 600/549 |
| 2008/0079628 A1 | 4/2008 | Wilkie et al. | |
| 2009/0139436 A1 | 6/2009 | Memory | |
| 2009/0325658 A1 | 12/2009 | Phelan et al. | |
| 2011/0248725 A1 | 10/2011 | Mukherjee | |
| 2012/0253611 A1 | 10/2012 | Zielke et al. | |
| 2014/0230580 A1 | 8/2014 | Dybro et al. | |
| 2014/0326066 A1 | 11/2014 | Mears | |
| 2014/0331631 A1 * | 11/2014 | Sauder | A01D 45/021 56/10.2 R |
| 2015/0293029 A1 | 10/2015 | Acheson et al. | |
| 2016/0330907 A1 * | 11/2016 | Anderson | A01D 41/1278 |
| 2017/0065464 A1 * | 3/2017 | Heil | A61F 13/42 |
| 2018/0058900 A1 | 3/2018 | Tevs et al. | |

FOREIGN PATENT DOCUMENTS

| | | |
|---|---|---|
| EP | 1714542 A1 | 10/2006 |
| JP | 6333296 A | 2/1988 |
| WO | 9849529 A1 | 11/1998 |

OTHER PUBLICATIONS

Milligan, Thomas A. Modem Antenna Design, Second Edition. John Wiley & Sons, 2005. p. 299-300.

Search Report issued in counterpart application No. EP 1718897.7, dated Feb. 22, 2018 (13 pages).

* cited by examiner

Attenuation dB

| Frequency | Free Air | Empty Cell | Water | Oil | Canola Seeds | Corn Kernels | Corn MOG |
|---|---|---|---|---|---|---|---|
| 4.463 GHz | -25 | -33 | -32 | -41 | - | - | - |
| 5.376 GHz | -32 | -34 | -34 | -40 | -40 | -45 | -35 |

FIG. 11

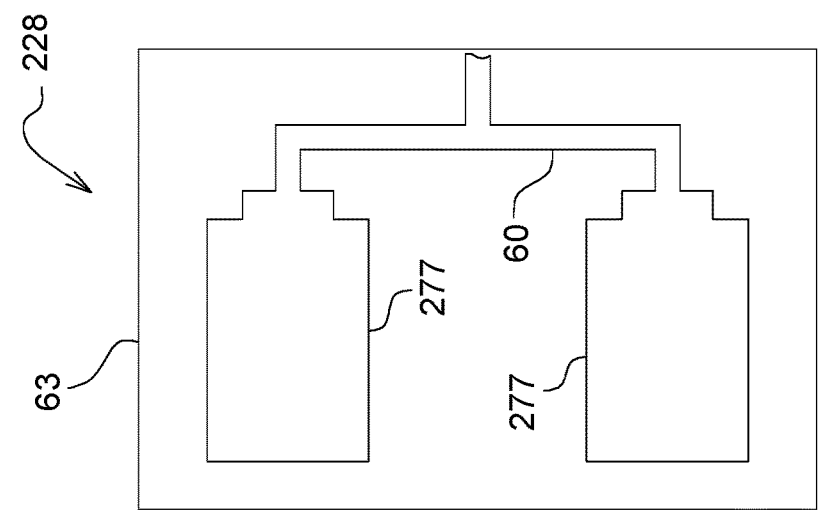
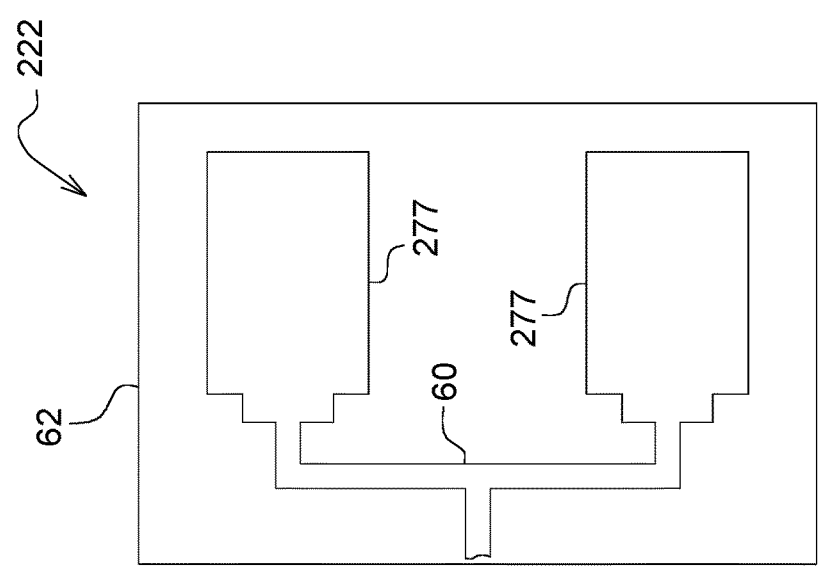
FIG. 13

MEASUREMENT DEVICE AND METHOD FOR ESTIMATING YIELD OF A HARVESTED CROP

RELATED APPLICATION

This document (including the drawings) claims priority and the benefit of the filing date based on U.S. provisional application No. 62/382,115, filed Aug. 31, 2016 under 35 U.S.C. § 119 (e), where the provisional application is hereby incorporated by reference herein.

FIELD

This disclosure relates to a measurement device and method for estimating a yield of a harvested crop.

BACKGROUND

Certain prior art yield monitors provide estimates of crop yield for an entire swath of a harvesting machine in a field of crop, rather than yields for one or more plant rows or sections of the crop within the swath. The resolution of such yield monitors is limited and lacks sufficiently accurate feedback for some agricultural management practices related to precise placement of crop inputs, such as seed, fertilizer, pesticide, fungicide, or herbicide, for specific plant rows or sections of crop within a field. Accordingly, to manage the precise placement of crop inputs and to conduct other agricultural management practices there is need for precisely estimating a yield of a harvested crop for a row or section of crop within the swath of harvesting machine.

SUMMARY

In accordance with one embodiment, a measurement device is capable of providing a precise estimate of the yield a harvested crop for a row or section of crop within the swath of harvesting machine. The measurement device comprises a transmitter for providing a transmitted signal at a frequency. A transmitting antenna comprises a radiating element separated from a first ground plane by a first dielectric layer. The transmitter is capable of providing the transmitted signal to the transmitting antenna.

A receiving antenna comprises a receiving element separated from a second ground plane by a second dielectric layer. The receiving antenna is arranged to receive the transmitted signal. A receiver is capable of receiving the transmitted signal from the receiving antenna. An electronic data processor is adapted to measure an observed parameter of the transmitted signal between the transmitting antenna and the receiving antenna to estimate the precise yield, where the observed parameter comprises observed attenuation, phase, or both of the transmitted signal, as received at the receiver.

BRIEF DESCRIPTION OF THE DRAWINGS

FIG. 11 is a chart of attenuation versus frequency for various types of harvested material or samples.

FIG. 13 is an alternate embodiment of a plan view of a transmitting antenna and a receiving antenna, where each antenna has a plurality of patch elements.

Like reference numbers in any two or more drawings indicate like elements, features, procedures or steps.

DETAILED DESCRIPTION

A harvesting machine may comprise a harvester or combine. A swath of a harvesting machine refers to the width of a harvesting head or cutter of a harvesting machine or the width of crop that the harvesting machine may harvest or cut in a single pass. For row crops, such as corn or soybeans, the swath may comprise multiple rows of plants or crop. For non-row crops, such wheat, oats or barley, the swath may comprise multiple sections or strips, where the sections may be generally linear or curved in accordance with the path of the harvesting machine.

In accordance with one embodiment, a measurement device 111 is capable of providing a precise estimate of the yield a harvested crop for a row or section of crop within the swath of harvesting machine. The measurement device comprises a transmitter 20 for providing a transmitted signal at a frequency to a transmitting antenna 22.

Figure 1:
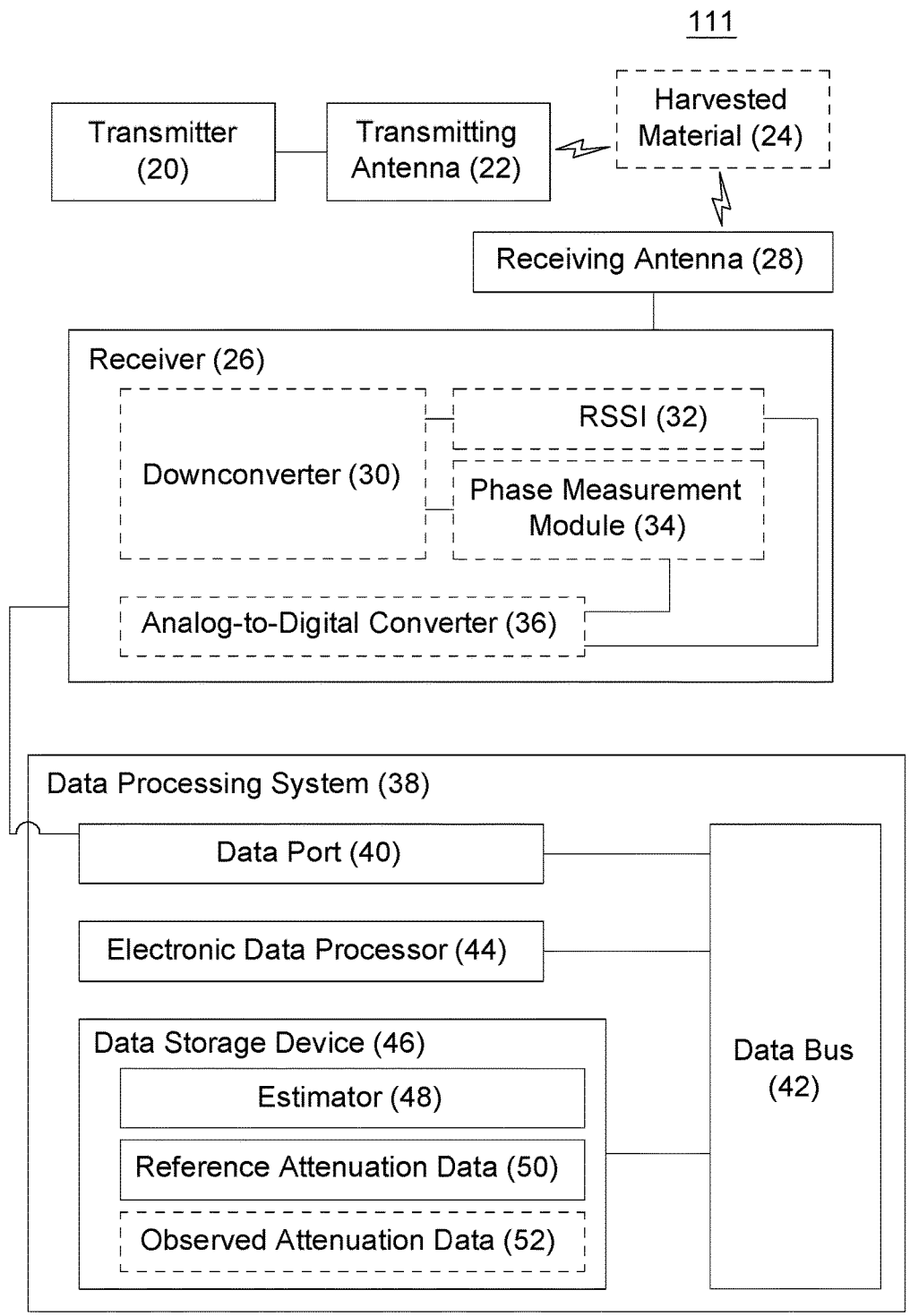
FIG. 1 is a block diagram of one embodiment of the measurement device.
Figure 4:
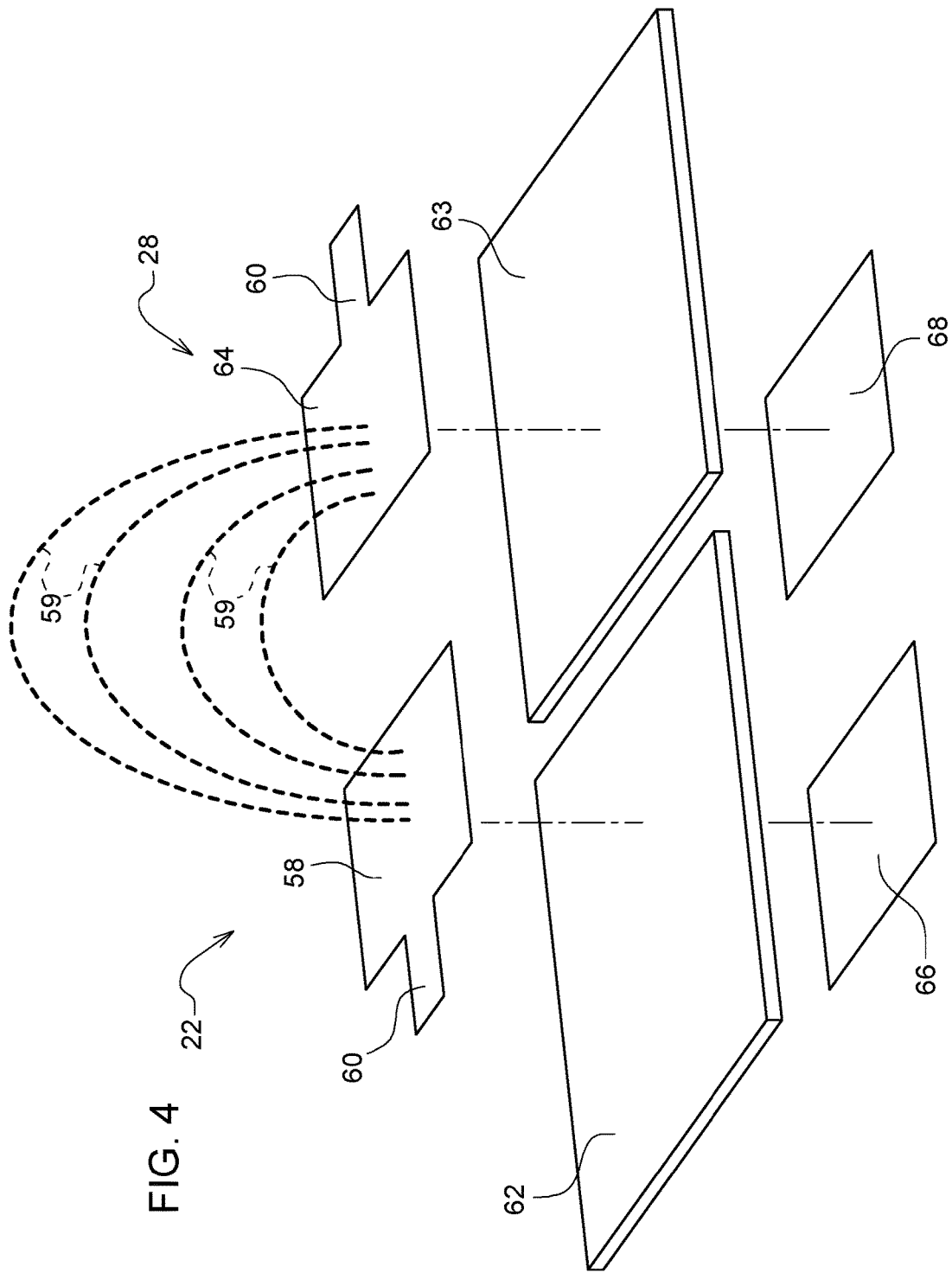
FIG. 4 is an exploded perspective view of one embodiment of transmitting antenna and a receiving antenna.
Figure 5:
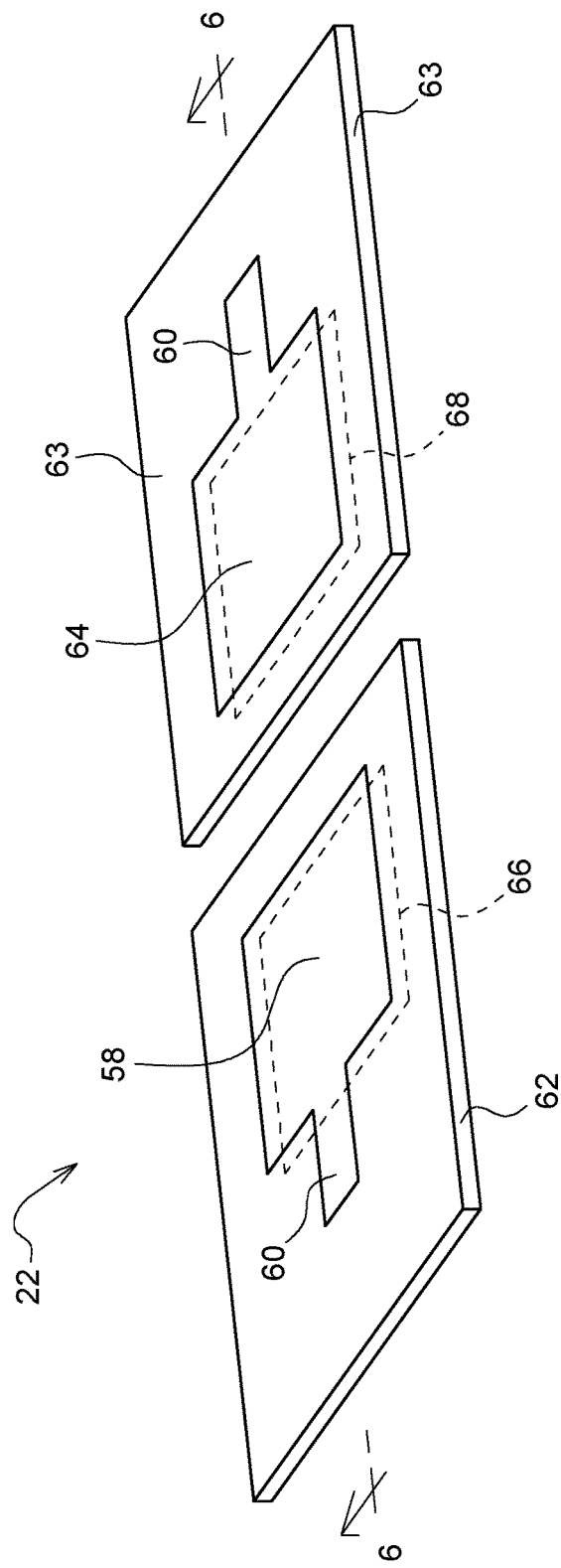
FIG. 5 is a perspective view of the transmitting antenna and receiving antenna of FIG. 4.
Figure 6:
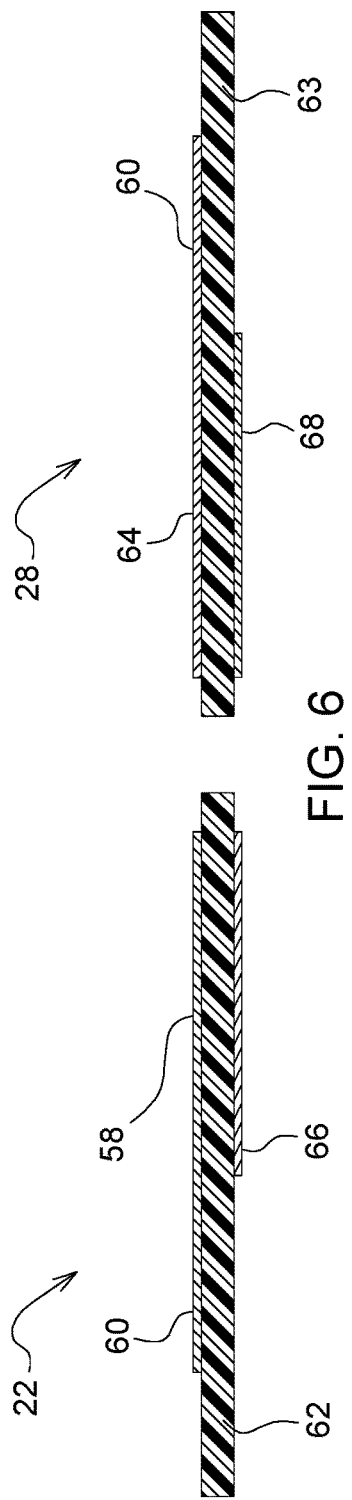
FIG. 6 is a cross-section view of the transmitting antenna and the receiving antenna of FIG. 6 along reference line 6-6 in FIG. 5.

As illustrated in FIG. 1 in conjunction with FIG. 4, FIG. 5 and FIG. 6, the transmitting antenna 22 comprises a conductive radiating element 58 (e.g. metallic patch antenna element) separated from a first ground plane 66 by a first dielectric layer 62. The radiating element 58 and the first ground plane 66 may be composed of a metal layer or metallic layer, such as copper or a copper alloy. The transmitter 20 provides the transmitted signal 59 or electromagnetic signal (e.g., between 100 MHz and 6 GHz) to the transmitting antenna 22 via a strip line, microstrip, coaxial cable, or other transmission line 60 (in FIG. 4). The transmitting antenna 22 has a transmission line 60 that is electrically connected to the radiating element 58.

As illustrated in FIG. 1 in conjunction with FIG. 4, FIG. 5 and FIG. 6, a receiving antenna 28 comprises a receiving element 64 (e.g., metallic patch antenna element) separated from a second ground plane 68 by a second dielectric layer 63. The receiving element 64 and the second ground plane 68 may be composed of a metal layer or metallic layer, such as copper or a copper alloy. The receiving antenna 28 is arranged to receive the transmitted signal. The transmitted signal be attenuated or changed in phase, or both attenuated and phase-changed, by intervening harvested material. Once the transmitted signal is received by the receiving antenna 28 or the receiver 26, it may be referred to as a received signal. The receiver 26 provides a received signal (e.g., derived from the transmitted signal) from the receiving element 64 via a strip line, microstrip, coaxial cable or other transmission line 60. The receiving element 64 has a transmission line that is electrically connected to the receiving element 64.

Although the radiating element 58 and the receiving element 64 may have various size and shape configurations, in one embodiment the radiating element 58 and the receiving element 64 each comprise a metallic rectangle (e.g., square) with a surface area of approximately one square inch. Further, the transmitter 20 may feed the transmitting antenna 22 with a circularly polarized transmitted signal.

In an alternate embodiment, the transmitting antenna 22 and the receiving antenna 28 may be replaced by horn antennae with horizontal polarization, vertical polarization, circular polarization, or other polarizations.

A receiver 26 is capable of receiving the transmitted signal or received signal from the receiving antenna 28. Once received by the receiving antenna 28 or receiver 26, or both, the transmitted signal may be referred to as a received signal in this document.

In one embodiment, the receiver 26 comprises a downconverter 30, a receiver signal strength indicator (RSSI) module 32, a phase measurement module 34 and an analog-to-digital converter 36. The above modules or components of the receiver 26 are indicated in dashed lines in FIG. 1 because they are optional and may be replaced by other configurations. A module may refer to software, electronics hardware, or both.

In one configuration, the receiver 26 comprises a microwave or radio frequency front end (e.g., low noise amplifier) for receiving the transmitted signal from the receiving antenna 28. The front end is coupled to a downconverter 30, such as one or more mixer stages to downconvert the received signal to a baseband signal or intermediate frequency signal for processing. The downconverter 30 is coupled to a receive signal strength indicator (RSSI) module 32 and a phase measurement module 34. The RSSI module 32 that may be associated with a discriminator (e.g., for a frequency modulation or phase modulated received signal). The RSSI module 32 can measure the signal strength of the received signal, which can be used to derive the attenuation from the transmitted signal transmitted from the transmitting antenna 22 because the signal strength and phase of the transmitted signal is known. The phase measurement module 34 measures the phase or carrier phase of the received signal, which can be used to derive the phase change of the transmitted signal transmitted from the transmitting antenna 22. For example, in one embodiment the phase measurement module 34 may use a local signal generator and one or more correlators to detect or measure a phase or carrier phase of the received signal. An analog-to-digital converter 36 converts analog data measurements of signal strength or attenuation and phase to digital measurements or representations.

The receiver 26 can provide or transmit the digital measurements or representations to the data processing system 38 via one or more data ports 40 of the data processing system 38. The data ports 40 refer to input/output data ports that may comprise transceivers and buffer memory, or other electronic hardware.

In one embodiment, an electronic data processor 44 comprises a microprocessor, a microcontroller, a digital signal processor, a programmable logic array, a field programmable gate array, an applicable specific integrated circuit, a logic circuit, a Boolean logic circuit, an arithmetic logic unit, or the like. An electronic data processor 44 is adapted to measure one or more of the following observed signal parameters to estimate the precise yield (e.g., on a row-by-row basis or on a section of a swath basis): (1) an observed attenuation of the transmitted signal (or received signal) between the transmitting antenna 22 and the receiving antenna 28, (2) observed phase change of the transmitted signal (or received signal) between the transmitting antenna 22 and receiving antenna 28. The electronic data processor 44 can measure the observed signal parameters (e.g., observed attenuation) between the transmitting antenna 22 and the receiving antenna 28 in various modes. During a calibration mode or reference mode, the electronic data processor 44 measures one or more of the following reference or baseline signal parameters: (1) a reference attenuation between the transmitting antenna 22 and the receiving antenna 28 when no harvested material 24 is present and (2) reference phase change between the transmitting antenna 22 and the receiving antenna 28 when no harvested material 24 is present. During an operational mode, the data processor 44 measures one or more of the following observed signal parameters: (1) attenuation of the transmitted signal (or received signal) between the transmitting antenna 22 and the receiving antenna 28 when harvested material 24 is present, (2) phase change of the transmitted signal (or received signal) between the transmitting antenna 22 and the receiving antenna 28 when harvested material 24 is present, (3) attenuation between the transmitting antenna 22 and the receiving antenna 28 when harvested material 24 comprises only secondary material (e.g., material other than grain or MOG) or a combination of harvested material 24 and secondary material, and (4) phase change between the transmitting antenna 22 and the receiving antenna 28 when harvested material 24 comprises only secondary material (e.g., material other than grain or MOG) or a combination of harvested material 24 and secondary material.

In one configuration, harvested crop or harvested material 24 comprises grain, maize, corn, oil seed, kernel, seed, soybeans, wheat, barley, oats, cotton, fiber, or other harvested material. For example, if the harvested material 24 is corn or maize, the secondary material may comprise stalks, husk and cobs of corn, weeds or other biomass plant material. In one embodiment, the secondary material may comprise edible forage material that can be fed to animals, although in other embodiments the secondary material may have high cellulose content that is suitable for various industrial uses, such as insulation, composting, or cellulosic fermentation. In some cases, the secondary material may sometimes include weeds or contaminants.

In some embodiments, the harvested material 24 or crop is composed of following main chemical constituent groups: (1) moisture (water), (2) oil, (3) protein, (4) starch/sugars, and (5) cellulose. For corn, the cob, the husk, and stalk contain cellulose and the grain contains sugar, starch, protein and oil. Among the above constituents, the measurement device can use the oil content as the basis for the measurement of the signal parameters.

In one configuration, the data storage device 46 comprises an estimator 48, reference attenuation data 50 and observed attenuation data 52. For example, the reference attenuation data 50 is collected in a reference mode or calibration mode when no harvested material 24 is present between the transmitting antenna 22 and the receiving antenna 28, where attenuation is less than when harvested material 24 is present between the transmitting antenna 22 and the receiving antenna 28. The data storage device 46 may also store reference phase data that is collected in a reference mode or calibration mode when no harvested material 24 is present between the transmitting antenna 22 and the receiving antenna 28. In contrast, the observed attenuation data 52 and observed phase data is collected when harvested material is present between the transmitting antenna 22 and the receiving antenna 28. Although observed phase data is not shown in FIG. 1, observed phase data may be stored in the data storage device, or a phase change or phase shift between the reference phase data and the observed phase data may be stored for one or more sampling periods or time intervals. Similarly, an attenuation change between observed attenuation data 52 and reference attenuation data 50 may be stored in the data storage device 46 for one or more sampling periods of time intervals.

Figure 10:
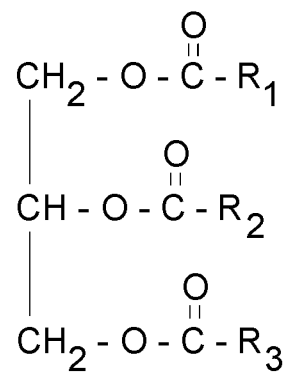
FIG. 10 is a diagram of the chemical structure of an oil, fatty acid or triglyceride content of a harvested crop.

FIG. 10 provides an illustrative representation of the chemical structure of oil, fatty acids or triglycerides in the corn. Depending on the harvest conditions (e.g., temperature and humidity), the moisture content in the harvested material 24 can vary significantly. Moisture tends to be present universally in corn ears, grain, and seeds and the material other than grain (MOG). Therefore, the moisture content level cannot be used to differentiate between the grain and the MOG in harvested material. Water/moisture shows wide variation in dielectric properties over temperature. Water/moisture also changes state once below the freezing point at which moisture content determination becomes a challenge.

Depending on the crop variety, oil can constitute about 6% to 12% of total grain content. Oil content in the grain resides primarily in the grain germ, seeds, and kernels. Oil content tends to be low or non-existent in MOG for all practical purposes. Moreover, in comparison to moisture, oil is largely an unbound constituent that doesn't exhibit widely varying characteristics over temperature and humidity. Accordingly, measurement of oil content of the harvested material provides a reliable basis for quantifying the sectional yield using radio frequency (RF) sensing methods.

Oil content in the grain, seeds and kernels is comprised mixtures of various triglycerides represented by chemical structure shown in FIG. 10, where, $R_1$, $R_2$ and $R_3$ are any hydrocarbon chains in which the C and O bonds exhibit resonance upon exposure to the transmitted signal within the frequency range of approximately 100 MHz to 6 GHz. Accordingly, in one embodiment, the transmitter 20 is adapted to transmit a frequency of the transmitted signal within the range of approximately 275 MHz to approximately 5.5 GHz. The above resonance property is exploited while utilizing the radio frequency spectrum to detect the oil content in grain, kernels and seeds, or the presence of the grain, kernel and seeds themselves.

In one embodiment, the attenuation of the transmitted signal (or received signal) is predominantly because of dielectric absorption losses of the harvested material 24, or the oil content with the dielectric material of the harvested material 24. During the calibration mode when no harvested material 24 is present, the attenuation is minimal and the receiver 26 receives a transmitted signal (or received signal) that meets or exceeds an attenuation threshold, reference attenuation, or reference signal strength. During an operational mode when predominately secondary harvested material 24, such as corn cobs, stalks, or other plant portions with high cellulose content are present, the attenuation of the transmitted signal (or received signal) is substantially equivalent to that of the calibration mode. However, during an operational mode, when harvested material 24 with material oil content (e.g., grain, seeds, and kernels) is present, the transmitted signal (or received signal) is significantly attenuated from the threshold and falls below the attenuation threshold, reference attenuation or reference signal strength. For example, illustrated in FIG. 11, the table shows attenuation in decibels along the horizontal axis 133 and the frequency of the transmitted signal of the transmitter 20 along the vertical axis 135. The attenuation of oil, canola seeds, corn kernels, exceeds the attenuation of secondary material (e.g., corn harvested material 24 other than grain) and the reference attenuation of free air or an empty cell.

During the operational mode, the phase change between the transmitted signal by the transmitter 20 and the received signal by the receiver 26 can depend upon the following factors: (1) spatial separation or spatial difference between the transmitting antenna 22 and the receiving antenna 28, (2) the frequency or wavelength of the transmitted signal, and (3) any phase change in the transmitted signal (or received signal) induced by the oil content or other properties of the harvested material 24.

In one embodiment, a data storage device 46 is coupled to the electronic data processor 44 via a data bus 42. In one example, the data storage device 46 comprises electronic memory, nonvolatile random access electronic memory, a magnetic storage device, an optical storage device, or the like. The data storage device 46 stores a measurement of a reference signal parameter, such as a reference signal strength, an attenuation threshold or reference attenuation, a reference phase change, or other reference data on signal parameters, when no harvested material 24 is present between the transmitting antenna 22 and receiving antenna 28.

The electronic data processor 44 is arranged to determine a difference or differences (e.g., an attenuation difference, a phase change difference or both) between the observed signal parameter of the transmitted signal parameter. For example, the electronic data processor 44 is arranged to determine an attenuation difference between the observed attenuation the reference attenuation. Similarly, the electronic data processor 44 can determine the phase difference between the observed phase change and the reference phase change. An estimator 48 uses the difference or differences to determine: (1) whether harvested material 24 is present during a sampling interval, and (2) the volume or mass of harvested material 24 that is present during a sampling interval for one or more rows of a harvesting machine in a field of crop, or a strip or section of a field. Further, an estimator 48 can use the difference or difference to determine whether material other than harvested material 24 is present and the precise yield of the harvested material 24 for a row, one or more rows, or a section or strip of field.

In one embodiment, the measurement device (111, 211, 311) operates within a frequency range of approximately 100 MHz to approximately 6 GHz, such as 275 MHz to approximately 5.5 GHz, to measure the absorption/transmission characteristics of harvested material 24 or oil content of the harvested material 24 (e.g., grain, kernel or seeds) with respect to the above frequency range within the radio frequency spectrum, the microwave spectrum, or both.

Figure 14:
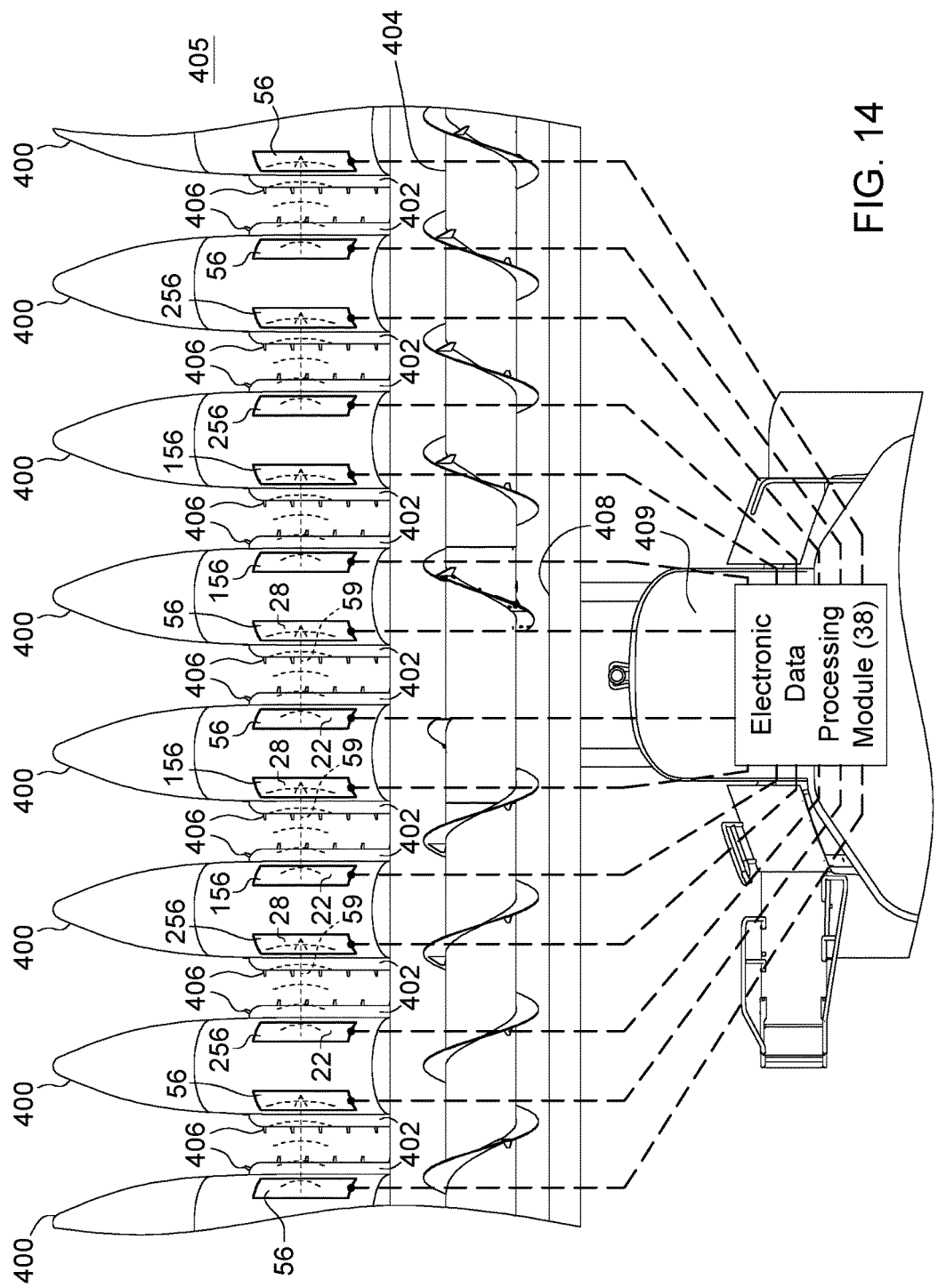
FIG. 14 shows a plan perspective view of a plurality of measurement devices installed on the header of the harvesting machine or combine.

As illustrated in FIG. 14, the transmitting antenna 22 is mounted on a header 405 of a harvesting machine and wherein the receiving antenna 28 is mounted on the header 405 and arranged to face the transmitting antenna 22 within a spatial zone that is arranged to receive a harvested material 24 during operation of the harvesting machine. For example, the spatial zone is associated with: (a) one more or strips of crop (e.g., harvested material 24) or (b) one or more rows of crop (e.g., harvested material 24) to facilitate estimation of the yield of crop or harvested material 24 within one or more strips or rows of crop on a row-by-row basis or a strip-by-strip basis.

In accordance with FIG. 1 and FIG. 14, if the transmitter 20, transmitting antenna 22, the receiving antenna 28, and the receiver 26 are secured to or mounted on one row of the header 405, the data processor 44 can provide an estimate of precise yield for that row, section or strip of field during a sampling interval. As used herein, the transmitter 20, transmitting antenna 22, receiving antenna 28 and receiver 26 for each row or section of a field may be referred to as a row unit (56 in FIG. 3). The header (405 in FIG. 14) may have one or more row units (56, 156, 256).

If the header 405 has a single row unit (e.g., indicated by elements 20, 22, 28 and 26 collectively in FIG. 1), the data processing system 38 may extrapolate or estimate the aggregate yield for an entire swath of the harvesting machine by multiplying the number of rows by the estimated yield from the single row with the row unit for one or more sampling intervals or for an entire field. However, if there are variances between plants or crops in the rows or strips in the field, the extrapolation or estimation may not be as accurate without also including a yield monitor for estimating an aggregate or total yield of the combine. Variances in the yield or performance of crops in the field may be associated with local variations in soil and levels of crop inputs received by specific plants, insect damage, or weed pressure, for instance.

Figure 2:
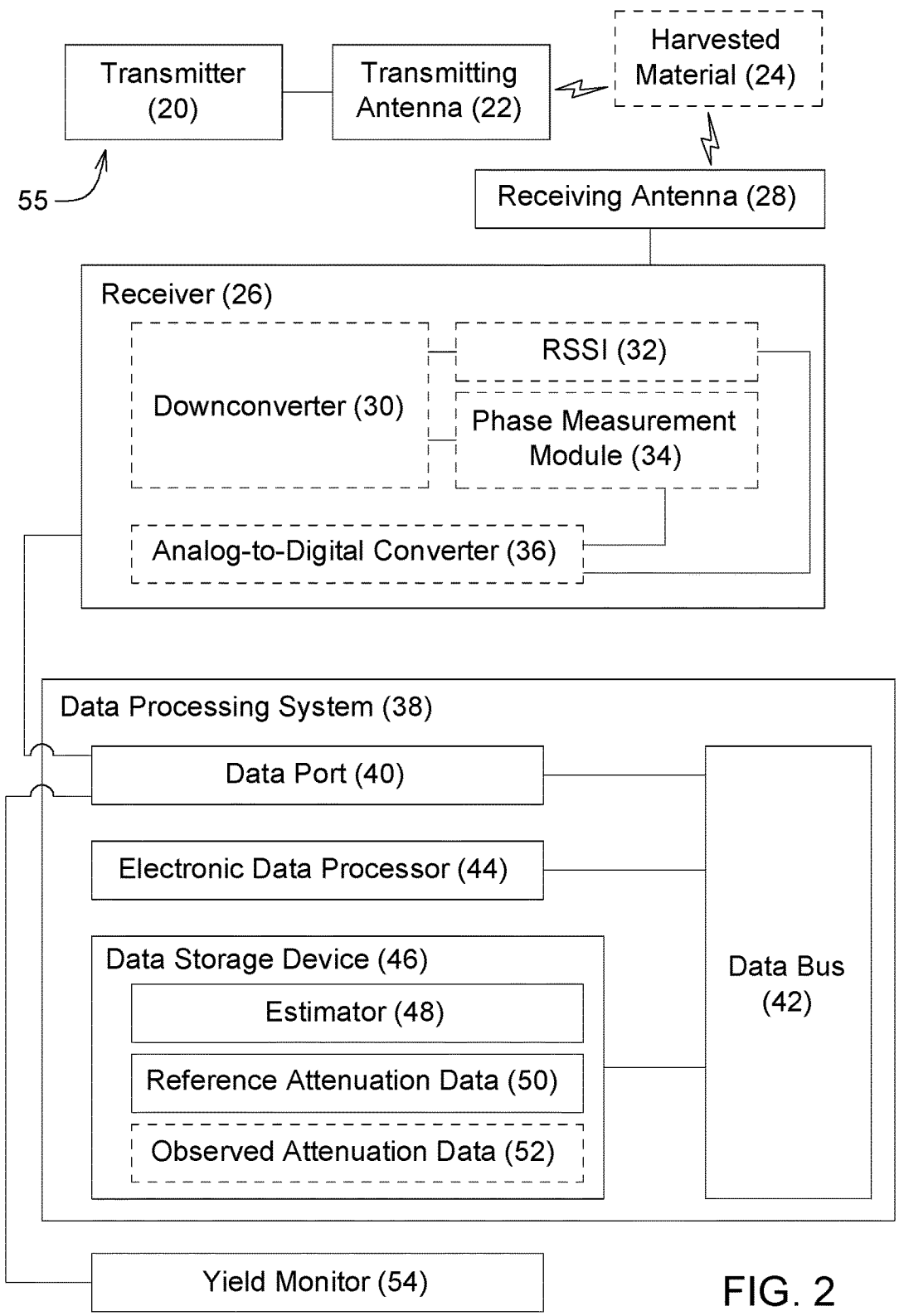
FIG. 2 is a block diagram of another embodiment of the measurement device with a yield monitor.
Figure 3:
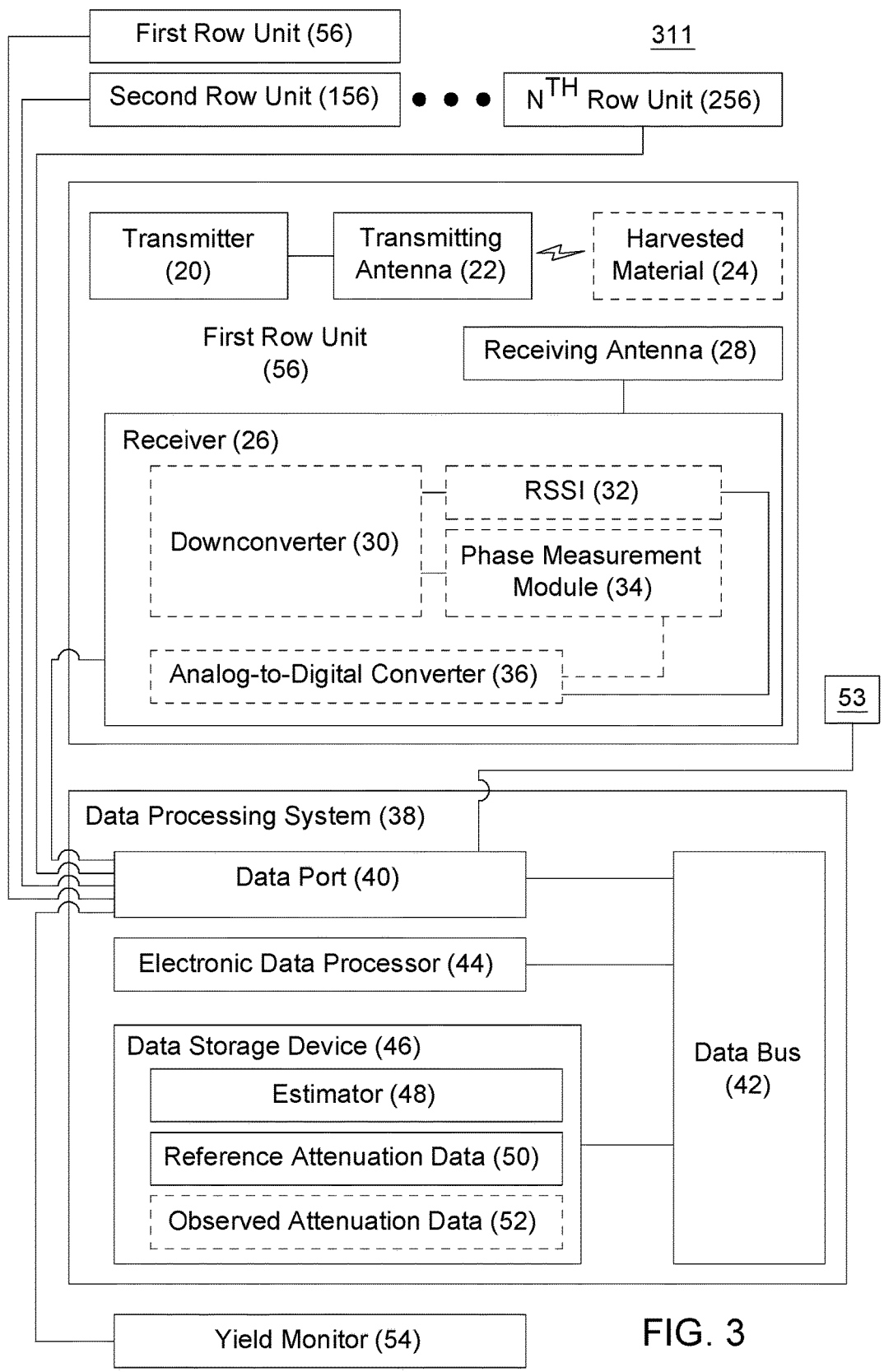
FIG. 3 is a block diagram of another embodiment of the measurement device with multiple row units for installation in the header of a harvester or combine.

In an alternate embodiment, the measurement device (111, 211 or 311) of FIG. 1, FIG. 2 or FIG. 3 may further comprise a location-determining receiver 53, such as satellite navigation receiver with differential correction for determining position (e.g., three dimensional coordinates) of the harvesting machine or the header of the harvesting machine, or movement data (e.g., velocity, acceleration, heading, yaw tilt and roll) during one or more sampling intervals. For example, location-determining receiver 53 may comprise a Global Positioning System (GPS) receiver (e.g., with differential correction or precise point positioning). The location-determining receiver 53 may provide position data, heading data, velocity data and acceleration data to the data processing system 38 via the data port 40 for one or more sampling intervals to estimate the distance or length (in the direction of travel of the harvester or combine) of the row of crop or plant material harvested during one or more sampling intervals. Alternately, instead of the location-determining receiver 53, a velocity sensor or ground speed sensor (e.g., based on radar or an odometer associated with a ground engaging wheel) of the harvester or combine provides relative position data, velocity data, or acceleration data for determining the distance traveled by the harvester or combine during one or more sampling intervals. In one embodiment, the data processing system 38 or the estimator 48 determines one or more of the following: (1) the total distance moved by a combine or harvester, (2) the harvested area of the field of harvester or combine during one or more sampling periods, (3) the associated volume or mass or harvested material for one or more rows to estimate yield per unit of land area. For example, the data processing system 38 or estimator 48 can estimate and associate each row of the harvester or combine with an observed, distinct estimate of yield per unit of land area (e.g., acre) of the harvested material 24, where the estimated yields may differ (or can be uniform if growing conditions permit) from row to row, from swath to swatch, or from zone to zone within the field.

Figure 7:
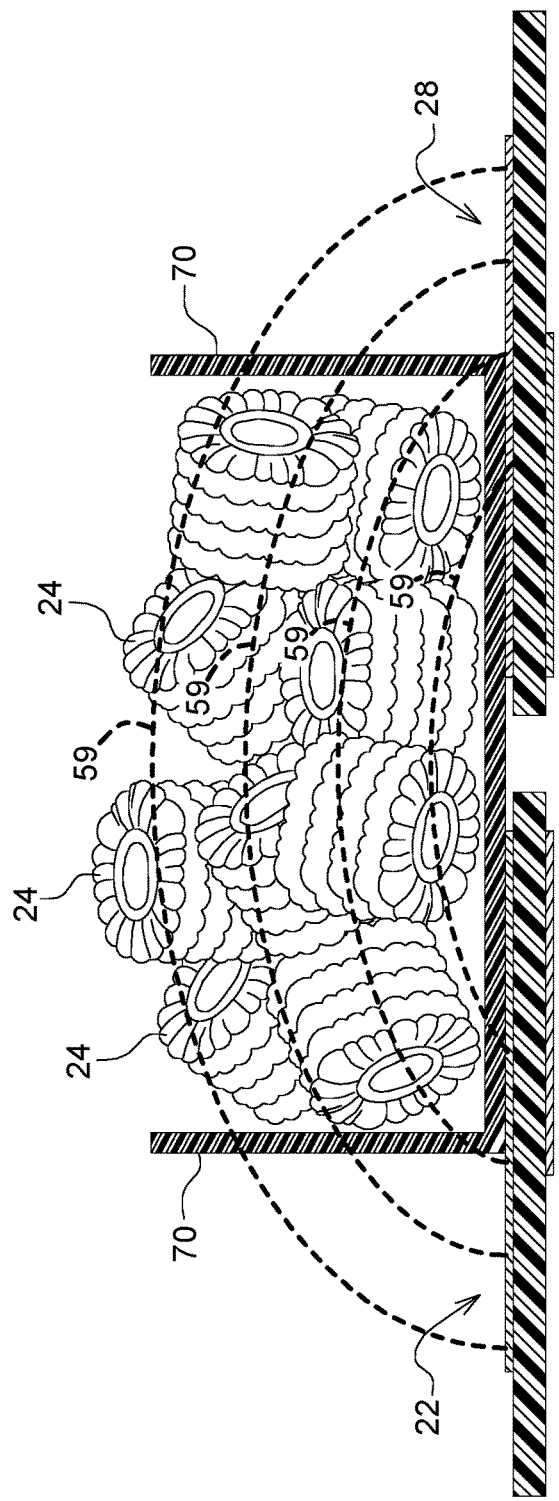
FIG. 7 is a cross-section view of the transmitting antenna and the receiving antenna similar to FIG. 6, except it further comprises a receptacle for holding samples of harvested material for evaluation.

The transmitting antenna 22 and receiving antenna 28 of FIG. 7 is similar to the transmitting antenna 22 and receiving antenna 28 of FIG. 4 through FIG. 6, inclusive, except a receptacle 70 is positioned in a path of a transmitted signal, received signal or electromagnetic field between the transmitting antenna 22 and the receiving antenna 28. In one embodiment as shown in FIG. 7, a receptacle 70 or channel is composed of dielectric material, positioned between the transmitting antenna 22 and the receiving antenna 28, and adapted to receive harvested material 24, or a mixture of harvested material 24 and other than grain (e.g., stalks and cobs for corn) for evaluation by the data processing system 38.

The measurement device 211 of FIG. 2 is similar to the measurement device 111 of FIG. 1, except the measurement device 211 of FIG. 2 further comprises a yield monitor 54. Like reference numbers in FIG. 1 and FIG. 2 indicate like elements.

Figure 15:
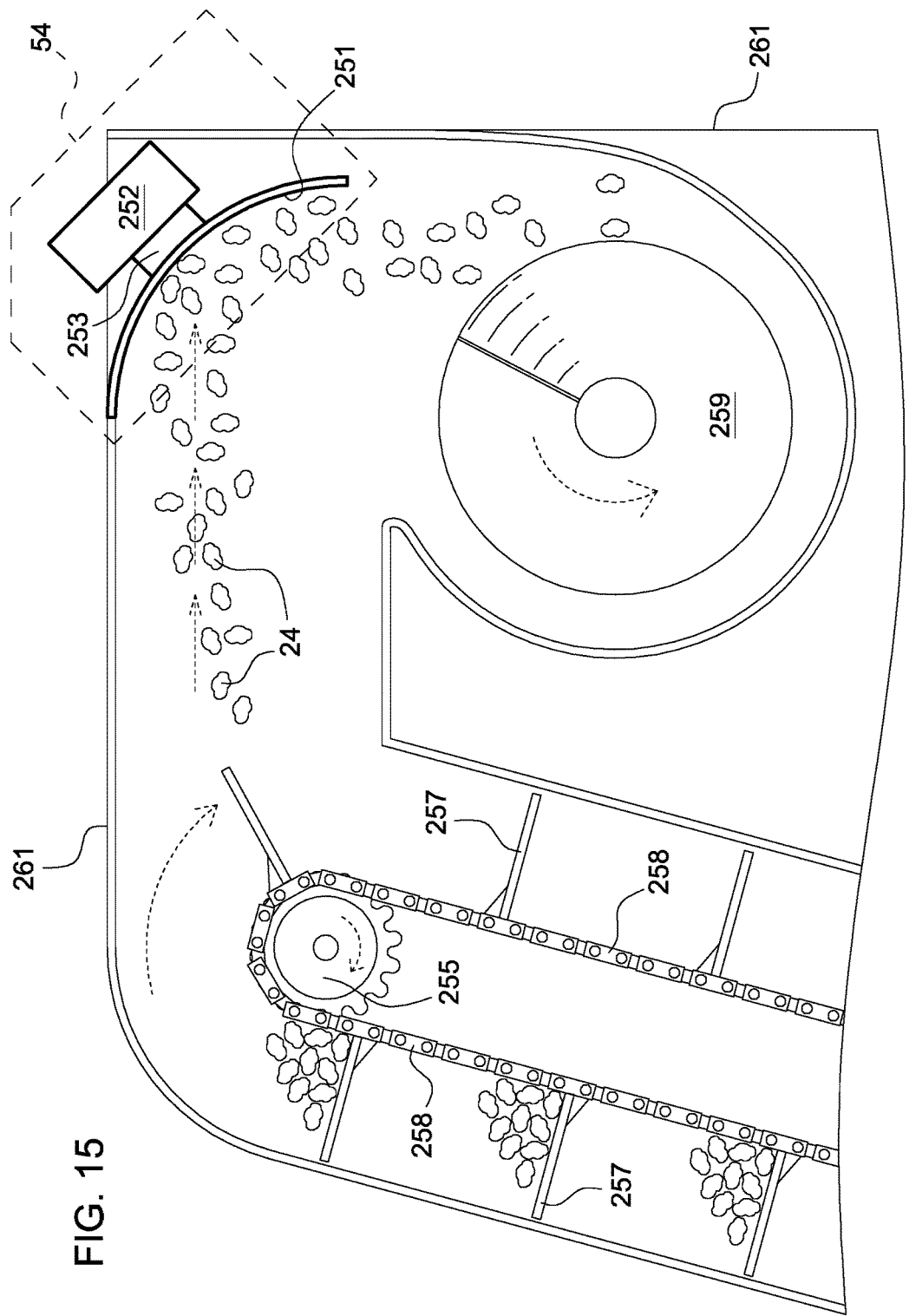
FIG. 15 shows a mass flow sensor installed in or around a clean grain elevator of a harvesting machine or combine.

In one embodiment, a yield monitor 54 is arranged for monitoring an aggregate yield of the harvesting machine with respect to an entire swath or width of the header of the harvesting machine. Further, the aggregate yield of the yield monitor 54 supports calibration the measurement device and facilitate pro-rata allocation of harvested material 24 for each row associated with a distinct or separate measurement device. In one embodiment, the yield monitor 54 may be installed in the clean grain elevator (261) of the harvesting machine or combine, as illustrated in FIG. 15, which is described later in this document.

The measurement device 311 of FIG. 3 is similar to the measurement device 211 of FIG. 2, except the measurement device 311 of FIG. 3 includes a plurality of row units (56, 156, 256) and a location-determining receiver 53. Like reference numbers indicate like elements throughout different drawings in this document.

In FIG. 3 and FIG. 14, a row unit (56, 156, 256) may be associated with each separate row of the header of the harvesting machine. As shown in FIG. 3, a first row unit 56, a second row unit 156 through an Nth row unit 256 was shown, where N is equal to a positive whole number or positive integer of the number of rows of the header or the harvesting machine. Each row unit (56, 156, 256) comprises a transmitter 20, transmitting antenna 22, a receiving antenna 28, and a receiver 26. As illustrated in FIG. 3, the data processing system 38 comprises a central processing system that accepts inputs from multiple row units (56, 156, 256). The data processing system 38 can determine or estimate yield for each row or section of the field based upon the data provided by a corresponding row unit on the harvesting machine. Further, the yield monitor 54 can provide aggregate yield data for the entire swath of the harvesting machines or all rows to compare against (e.g., for error checking and consistency) the output yield data for each row or sectional yield of one or more row units (56, 156 and 256) for a sampling interval.

Figure 8:
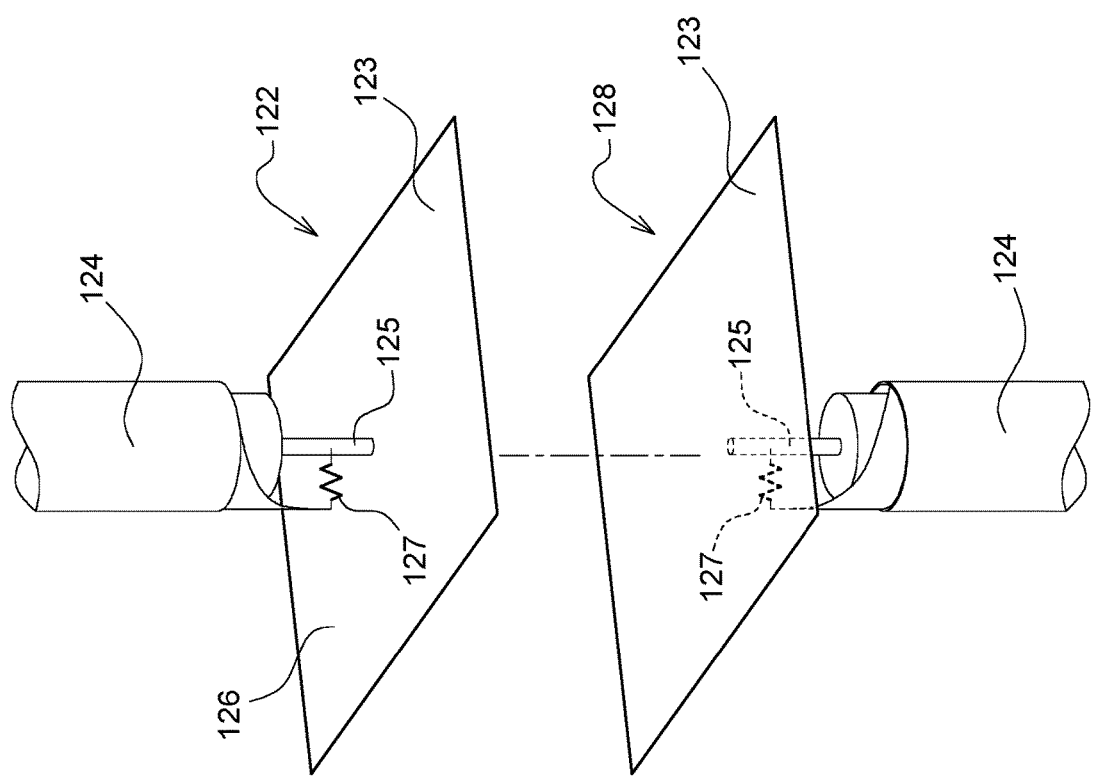
FIG. 8 is a perspective view of an alternate embodiment of a transmitting antenna and a receiving antenna.

FIG. 8 shows an alternate embodiment of a transmitting antenna 122 and a receiving antenna 128, which can be substitute for the transmitting antenna 22 and receiving antenna 28 of FIG. 1 through FIG. 3, inclusive, or in any embodiment in this document. Here, the transmitting antenna 122 and the receiving antenna 128 each comprise a plate or generally planar conductive member 123. As illustrated the conductive member 123 comprises a generally rectangular conductive member, although the conductive member 123 may be shaped as a polygon, ellipse, circle or with another shape. For impedance matching purposes the center conductor 125 of a coaxial cable 124 may be connected to about or near a central portion 126 (e.g., geometric center) of the conductive member 123, where a impedance matching element, such as a resistor, may be connected between the center conductor 125 and the ground or outer conductor 928 of the coaxial cable 124.

Figure 9:
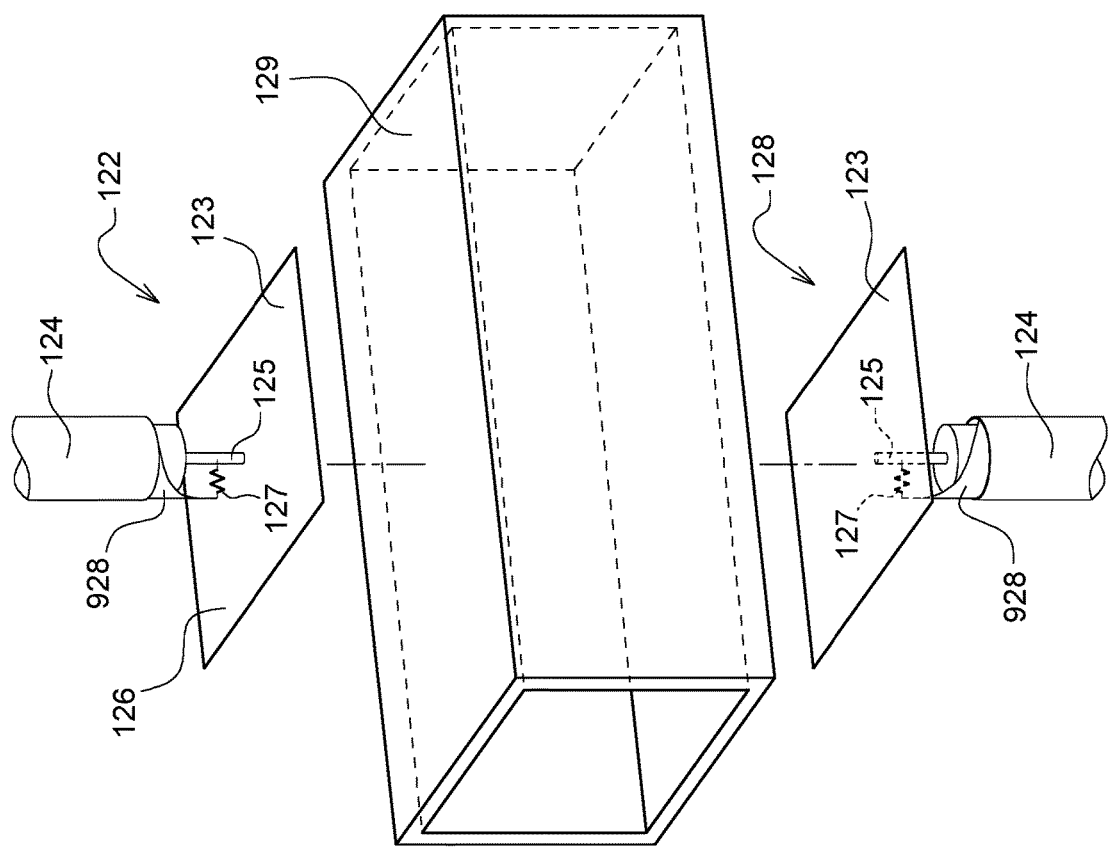
FIG. 9 is a perspective of an alternate embodiment of a transmitting antenna and receiving antenna that are associated with a rectangular dielectric channel or chamber for holding or conveying samples of harvested material for evaluation.
Figure 16:
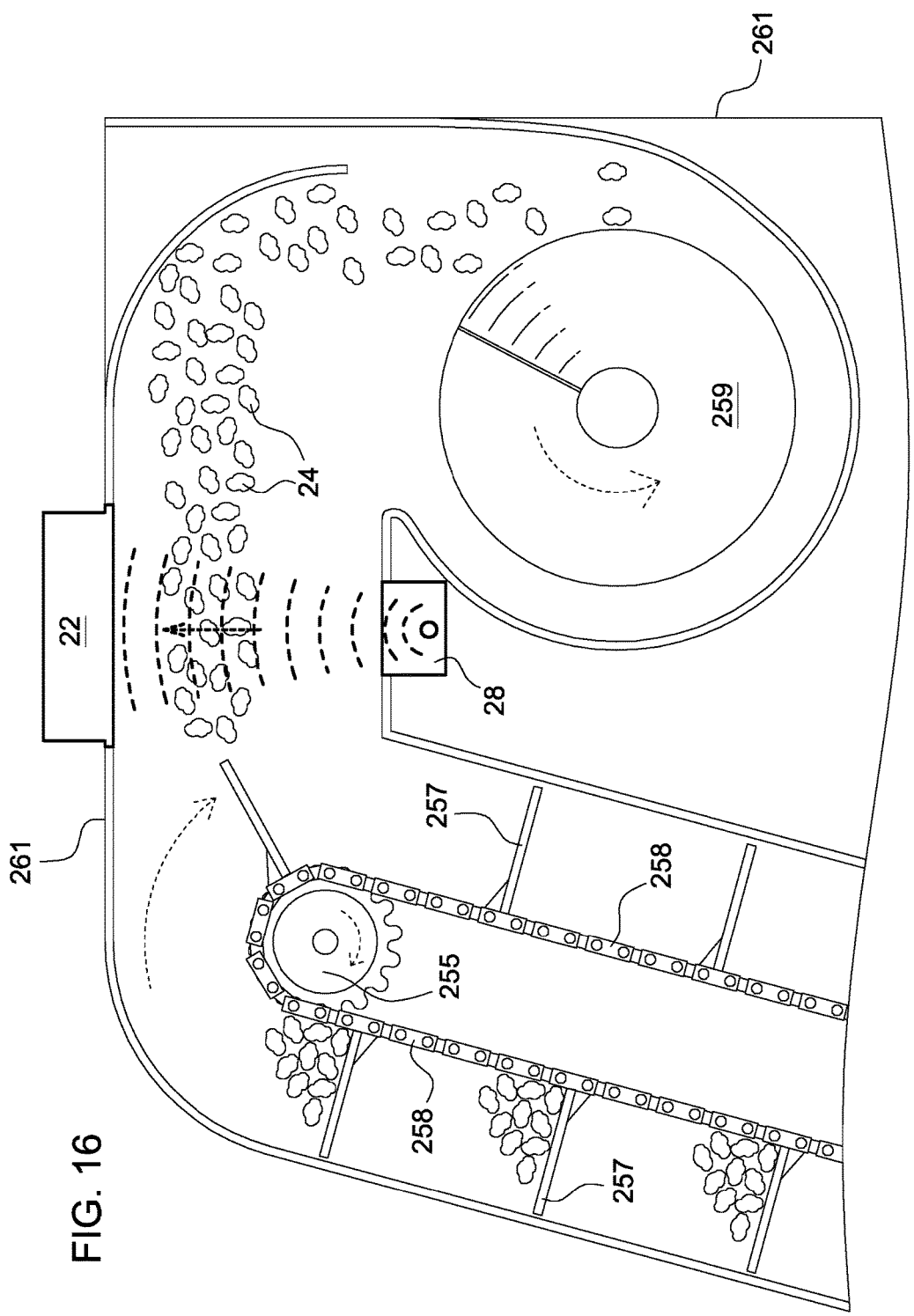
FIG. 16 shows a transmitting antenna and a receiving antenna installed in or around a clean grain elevator of a harvesting machine or combine.

FIG. 9 is similar to FIG. 8 except a hollow dielectric conduit 129 is interposed between the transmitting antenna and 122 and the receiving antenna 128. For example, the hollow dielectric conduit 129 may comprise a portion of a clean grain elevator 261 of harvesting machine or a combine, as is illustrated in FIG. 16, except FIG. 16 uses analogous antennae (22, 28). In one embodiment, the transmitting antenna 122 and the receiving antenna 128 are integrally formed on a hollow dielectric conduit 129 for conveying or carrying harvested material 24. For example, the hollow dielectric conduit 129 has a rectangular cross section where conductive members 123 or antennae (122, 128) are disposed on opposite sides of the conduit 129. In one embodiment, the conductive members 123 can comprise copper or a copper alloy.

Figure 12:
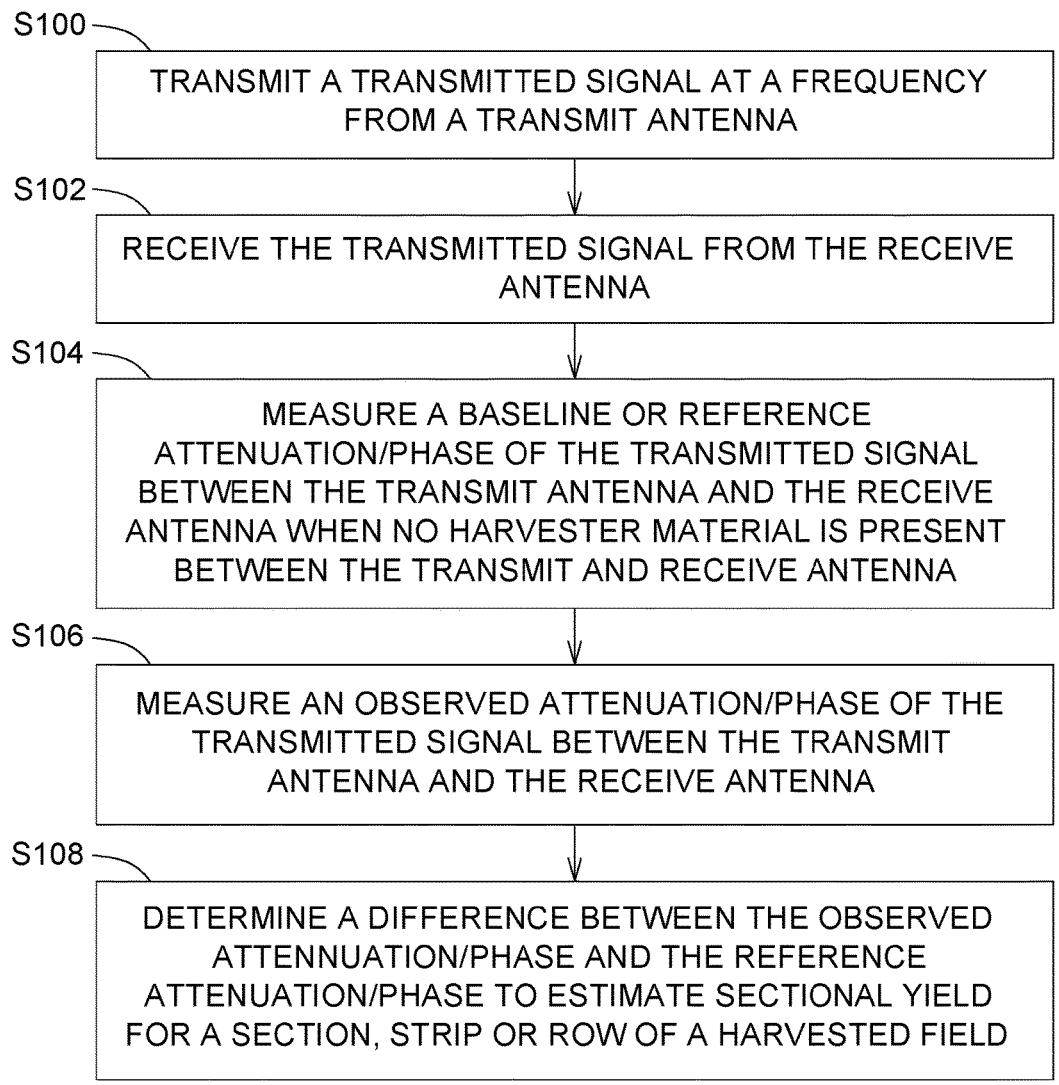
FIG. 12 is a flow chart of method for measuring a yield of harvested material in a row or section (e.g., sub-swath section) of the field.

FIG. 12 is a flow chart of method for measuring a yield of harvested material 24 in a row or section (e.g., sub-swath section) of the field. The method of FIG. 12 begins in step S100.

In step S100, a transmitter 20 transmits a transmitted signal at a frequency from a transmitting antenna (e.g., 22, 122, 222). For example, in one embodiment the transmitting antenna (e.g., 22, 122, 228) is secured to or mounted on a header of a harvesting machine. In one embodiment, the frequency comprises a frequency within the range of approximately 275 MHz to approximately 5.5 GHz.

In step S102, a receiver 26 receives the transmitted signal from the receiving antenna (e.g., 28, 128, 228), securing a transmitting antenna (22, 122, 228) to a header of a harvesting machine. In one embodiment, the receiving antenna (28, 128, 228) is secured to or mounted on the header, where the receiving antenna (28, 128, 228) is arranged to face the transmitting antenna (22, 122, 228) within a spatial zone that is arranged to receive a harvested material 24 during operation of the harvesting machine. The spatial zone is associated with a one or strips of crop or rows of crop to facilitate estimation of the yield within a strip or row of crop.

In step S104, a data processing system 38 or a data processor 44 measures or obtains a baseline or reference parameter of the transmitted signal between the transmitting antenna (22, 122, 222) and the receiving antenna (28, 128, 228) when no harvested material 24 is present between the transmitting and receiving antenna (28, 128, 228), where the reference parameter comprises reference attenuation, a reference phase, or both. The data processor 44 may measure the baseline or reference parameter or may access or retrieve a previously stored reference parameter of the transmitted signal (or received signal).

In step S106, the data processing system 38 or data processor 44 measures or obtains an observed parameter of the transmitted signal (or received signal) between the transmitting antenna (22, 122, 222) and the receiving antenna (28, 128, 228), where the observed parameter comprises observed attenuation, an observed phase, or both. For example, the data processing system 38 or data processor 44 measures the dynamic transmission/attenuation of radio frequency energy while harvesting of the harvested material 24 during a series of sampling intervals that are associated with corresponding location data for the combine or harvesting machine from a location-determining receiver (e.g., satellite navigation receiver or Global Positioning System (GPS) receiver with or without differential correction, or precise point positioning).

In one example, a receptacle or channel composed of dielectric material is positioned between the transmitted antenna and the receiving antenna (28, 128, 228), and adapted to receive harvested material 24, although when installed on a header 405 (FIG. 14) of a harvesting machine, the shoes 400 may form the channel.

In step S108, the data processor 44 or estimator 48 determines one or more differences (e.g., attenuation difference, phase difference or both) between the observed parameter (e.g., observed attenuation, observed phase, or both) and the reference parameter (e.g., reference attenuation, reference phase, or both) to estimate one or more of the following: (1) a sectional yield for a section, or strip of a harvested field, or portion thereof (e.g., zone), or (2) one or more rows of a harvested field, or a portion thereof (e.g., zone). If harvested material, such as grain or oil seed, is present, the attenuation difference exceeds an attenuation threshold that indicates that harvested material 24 is present within a row, section or strip. For example, the data processor 44 or estimator 48 processes the observed attenuation as a function of mass flow of the harvested material 24 to estimate the sectional yield of a section, strip or one or more rows of the harvested crop during a sampling interval.

The measurement device (111, 211, 311) is capable of measuring the yield of one or more rows of a crop during a sampling interval at a corresponding specific field location or zone indicated by a location-determining receiver. The attenuation difference increases or tends to increase with increased yield in any row or section that is harvested. For example, a higher attenuation than a target threshold indicates a greater yield for a row (or set of rows) during a sampling interval, and a lower attenuation than a target threshold differences indicates a lesser yield for a row (or set of rows) during a sampling interval. In one embodiment, the target threshold can be set to an average, mean or mode yield based on historic data for a particular field, farm, county, region or collected data from the same growing season for the particular field, farm, county or region. If the harvested material is contaminated with or contains material other than grain or oilseed, the attenuation measurements will be lower than attenuation measurements for harvested material that is predominately or completely grain, oil seed or harvested material 24 with material oil content.

Step S108 may be carried out by various techniques, which may be applied alternately or cumulatively.

Under a first technique, a mass flow sensor 54 measures the mass or volume of the harvested material 24 for the harvested crop for the entire swath of the vehicle or entire header during a sampling interval. Further, the data processor 44 or estimator 48 calibrates the estimated sectional yield based on the measurement mass flow of the mass flow sensor 54. Under the first technique, the mass flow sensor may be mounted on or associated with a clean elevator (261 in FIG. 15) or bypass channel associated with the clean elevator 261 of a combine or harvesting machine, for instance. The mass flow sensor 54 provides the total mass or volume of the harvested material 24 for the entire swath or all rows of crop within the swath for a particular sampling interval; hence, can be compared to the sum of the harvested material 24 estimated by the data processor 44 from data of each row unit (56, 156, 256) for the same sampling interval.

Under a second technique, if a row unit (56, 156 or 256) is not operational, the mass flow sensor 54 can provide a backup estimate for that particular row based upon the difference between total mass or volume of harvested material 24 for the entire swath less the yield estimate for the remaining rows with active row units.

Under a third technique, the mass flow sensor 54 can monitor an aggregate yield of the harvesting machine with respect to an entire swath or width of the header 405 or harvesting machine to calibrate data from one or more row units (56, 156, 256). For example, the data processor 44 or estimator 48 can facilitate pro-rata allocation of the yield of harvested material 24 for each row associated with a distinct or separate row unit (56, 156, 256).

Under a fourth technique, based on the difference or differences, the data processor 44 or estimator 48 determines whether harvested material 24 is present during a sampling interval.

Under a fifth technique, based on the difference or differences, the data processor 44 or estimator 48 determines whether material other than harvested material 24 is present.

FIG. 13 shows a transmitting antenna 222 and a receiving antenna 228 that can be substituted for the transmitting antenna 22 and the receiving antenna 28 of FIG. 5 for any embodiments set forth in this document. Here, the transmitting antenna 222 comprises multiple conductive antenna elements 277 (e.g., patch antenna elements) that are interconnected with conductive traces, stripline, microstrip, or other transmission lines 60. Similarly, the receiving antenna comprises 228 multiple conductive antenna elements 277 (e.g., path antenna elements) that are interconnected with conductive traces, stripline, microstrip or other transmission lines 50. The multiple conductive elements 277 may support a broader bandwidth, a narrower radiation beam width (e.g., half-power beam width), or both of the transmitting antenna 222, the receiving antenna 228 or both than is possible with a single conductive element 277, or similar to conductive elements (58, 63) in FIG. 4 through FIG. 6, inclusive.

As illustrated in FIG. 14, a row unit (56, 156, 256) is associated with each space or gap between the header shoes 400 of the header 405. In one embodiment, a rotating gathering chain 402 with spaced paddles 406 or protrusions collects harvested materials 24 and stalks for feeding the feeder house 408 of the harvester 409 or combine. The feeder house 408 comprises an opening associated with an auger 404 for intake of the harvested material 24.

In one embodiment, each row unit (56, 156, 256) is split between two shoes 400 that form an intake channel for the harvested material 24. A first shoe is associated with a transmitter 20 and a transmitting antenna 22, whereas a second shoe adjacent to the first shoe is associated with a receiving antenna 28 and a receiver 26. Although eight shoes 400 and eight corresponding row units (56, 156, 256) are associated with the header 405, any number of shoes 400 and row units (56, 156, 256) may be used in practice and depends upon the header size of the harvesting machine. In one embodiment, the row units (56, 156, 256) are coupled to the electronic data processing system 38 via one or more transmission lines.

In an alternate embodiment, the row unit may only include a transmitting antenna 22 and a receiving antenna 28 and the data processing system 38 may be associated with a plurality of transmitters 20 and receivers 26 (or a multi-channel transmitter and multi-channel receiver) to support each receiving antenna 28 and transmitting antenna 22.

In one embodiment, the transmitting antenna 22 is mounted on a header 405 of a harvesting machine and the receiving antenna 28 is mounted on the header 405 and arranged to face the transmitting antenna 22 within a spatial zone that is arranged to receive a harvested material 24 during operation of the harvesting machine. For example, the spatial zone is associated with a one or strips of crop or rows of crop to facilitate estimation of the yield within a strip or one or more rows of crop by the electronic data processing system 38.

FIG. 15 shows a mass flow sensor 54 installed in a clean grain elevator of a harvesting machine or combine. A cross section of the clean elevator 261 is shown in which a chain 258 or belt with paddles 257 lifts grain or harvested material 24 from a storage container (e.g., grain tank) toward a mass flow sensor 54. The chain 258 or belt may be driven by a gear, pulley or cog, such as member 255. In one embodiment, the mass flow sensor 54 is mounted on a housing, wall or passageway associated with the clean grain elevator 261. In one configuration, the mass flow sensor 54 comprises movable plate 251 or movable strike plate that is struck or displaced by harvested material 24. The plate 251 is coupled to a piezoelectric sensor 253, such as a piezoresistive sensor, that changes an electrical parameter or resistance in response to the application for force to the plate. Sensor electronics 252 are coupled to the piezoelectric sensor 253 to measure or detect the change in the electrical parameter during one or more sampling intervals.

The mass flow sensor 54 receives grain or harvested material 24 from all of the rows of the header; hence, provides an aggregate yield of the harvesting machine or combine for any sampling period. The mass flow sensor 54 may be coupled to the electronic data processing system 38 for processing or use in conjunction with sectional yield data from one or more row units (56, 156, 256). An unloading auger 259 can convey or unload harvested material 24 from the combine, harvesting machine or forage harvesting via a spout.

FIG. 16 shows a transmitting antenna 22 and a receiving antenna 28 installed in a clean grain elevator 261 of a harvesting machine or combine, as an alternate embodiment of a mass flow sensor for measuring the aggregate harvested material harvested by the harvester or combine. Like reference numbers in FIG. 15 and FIG. 16 indicate like elements.

Having described one or more embodiments in this disclosure, it will become apparent that various modifications can be made without departing from the scope of the invention as defined in the accompanying claims. For example, one or more of any dependent claims set forth in this document may be combined with any independent claim to form any combination of features set forth in the appended claims, and such combination of features in the claims are hereby incorporated by reference into the specification of this document.

The following is claimed:

1. A measurement device comprising:
    a transmitter for providing a transmitted signal at a frequency;
    a transmitting antenna comprising a radiating element separated from a first ground plane by a first dielectric layer, the transmitter providing the transmitted signal to the transmitting antenna;

a receiving antenna comprising a receiving element separated from a second ground plane by a second dielectric layer, the receiving antenna arranged to receive the transmitted signal;

a receiver for receiving the transmitted signal from the receiving antenna; and an electronic data processor for measuring an observed parameter of the transmitted signal between the transmitting antenna and the receiving antenna to estimate a yield of a harvested crop for a row or section of crop within the swath of a harvesting machine, where the observed parameter comprises observed attenuation, phase or both.

2. The measurement device according to claim 1 further comprising:

a data storage device for establishing or storing a measurement of a reference parameter when no harvested material is present between the transmitting antenna and receiving antenna;

the electronic data processor arranged to determine a difference between the observed parameter the reference parameter, where the reference parameter comprises reference attenuation, reference phase or both.

3. The measurement device according to claim 1 further comprising:

an estimator for using the difference to determine whether harvested material is present during a sampling interval.

4. The measurement device according to claim 1 further comprising:

an estimator for using the difference to determine whether material other than harvested material is present.

5. The measurement device according to claim 1 further comprising:

a receptacle or channel composed of dielectric material, positioned between the transmitted antenna and the receiving antenna, and adapted to receive harvested material.

6. The measurement device according to claim 1 wherein the transmitting antenna is mounted on a header of a harvesting machine and wherein the receiving antenna is mounted on the header and arranged to face the transmitting antenna within a spatial zone that is arranged to receive a harvested material during operation of the harvesting machine.

7. The measurement device according to claim 6 wherein the spatial zone is associated with a one or strips of crop or rows of crop to facilitate estimation of the yield within a strip or row of crop.

8. The measurement device according to claim 6 further comprising:

a yield monitor for monitoring an aggregate yield of the harvesting machine with respect to an entire swath or width of the header or harvesting machine to calibrate the measurement device and facilitate pro-rata allocation of harvested material for each row associated with a distinct or separate measurement device.

9. The measurement device according to claim 1 wherein the frequency comprises a frequency within the range of approximately 275 MHz to approximately 5.5 GHz.

10. A method for measuring harvested material, the method comprising:

transmitting a transmitted signal at a frequency from a transmitting antenna;

receiving the transmitted signal from the receiving antenna;

measuring a baseline or reference parameter of the transmitted signal between the transmitting antenna and the receiving antenna when no harvested material is present between the transmitting and receiving antenna, where the reference parameter comprises reference attenuation, phase or both;

measuring an observed parameter of the transmitted signal between the transmitting antenna and the receiving antenna, where the observed parameter comprises observed attenuation, phase or both; and determining a difference between the observed parameter and the reference parameter to estimate sectional yield for a section, strip or row of a harvested field.

11. The method according to claim 10 further comprising:

measuring a mass flow of the harvested material by a mass flow sensor;

calibrating the estimated sectional yield based on the measurement mass flow.

12. The method according to claim 10 further comprising:

based on the difference, determining whether harvested material is present during a sampling interval.

13. The method according to claim 10 further comprising:

based on the difference, determining whether material other than harvested material is present.

14. The method comprising according to claim 10 further comprising:

positioning a receptacle or channel composed of dielectric material between the transmitted antenna and the receiving antenna, and adapted to receive harvested material.

15. The method according to claim 10 wherein:

securing a transmitting antenna to a header of a harvesting machine;

securing a receiving antenna to the header, where the receiving antenna is arranged to face the transmitting antenna within a spatial zone that is arranged to receive a harvested material during operation of the harvesting machine.

16. The method according to claim 15 wherein the spatial zone is associated with a one or strips of crop or rows of crop to facilitate estimation of the yield within a strip or row of crop.

17. The method according to claim 15 further comprising:

monitoring an aggregate yield of the harvesting machine with respect to an entire swath or width of the header or harvesting machine to calibrate the method and facilitate pro-rata allocation of harvested material for each row associated with a distinct or separate method.

18. The method according to claim 10 wherein the frequency comprises a frequency within the range of approximately 275 MHz to approximately 5.5 GHz.

* * * * *